Figure 1:
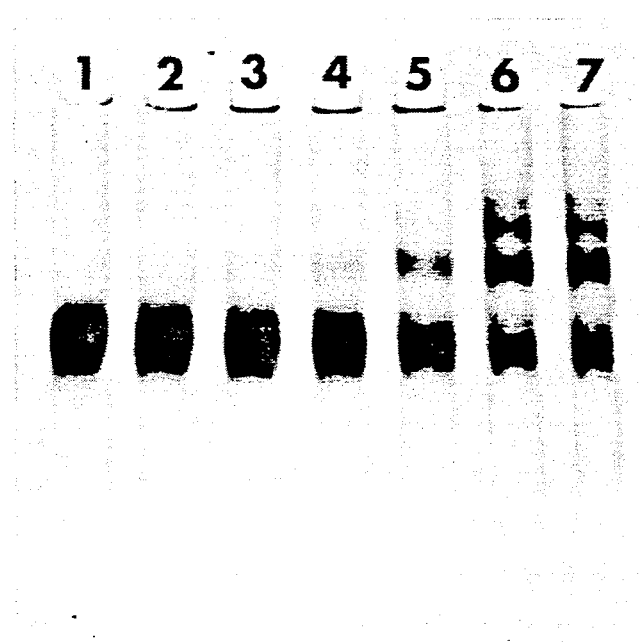

United States Patent [19]

Barbaric et al.

[11] Patent Number: 5,258,501
[45] Date of Patent: Nov. 2, 1993

[54] STABILIZATION OF GLYCOPROTEINS

[76] Inventors: Slobodan Barbaric, Selska 34, 41000 Zagreb, Yugoslavia; Branko Kozulic, Georg Kempfstrasse 7, 8046 Zürich, Switzerland

[21] Appl. No.: 844,826

[22] Filed: Mar. 2, 1992

Related U.S. Application Data

[63] Continuation-in-part of Ser. No. 438,642, Nov. 20, 1989, abandoned.

[30] Foreign Application Priority Data

Nov. 25, 1988 [GB] United Kingdom ............... 8827717

[51] Int. Cl.$^5$ ............................................ C07K 15/14
[52] U.S. Cl. ........................... 530/395; 435/177; 435/188; 435/190; 435/191; 435/201; 530/391.7; 530/391.9; 530/397
[58] Field of Search ............ 530/395, 397, 391.7, 530/391.9; 514/8; 435/177, 188, 201, 190, 191

[56] References Cited

U.S. PATENT DOCUMENTS

| | | | |
|---|---|---|---|
| 4,419,444 | 12/1983 | Quash | 435/188 |
| 4,911,911 | 3/1990 | Casellas et al. | 514/8 |
| 4,911,912 | 3/1990 | Casellas et al. | 514/8 |

OTHER PUBLICATIONS

Bayer et al, Analytical Biochemistry, 161, 123-131 (1987).
Eur. J. Biochem. 147, 197-206(1985), Thorpe et al.
Biochimica et Biophysica Acta. 842, 12-21 (1985).
Heimgartner et al, J. of Immunoligical Methods, vol. 132, 1990, pp. 239-245.
Heimgartner et al. Analytical Biochemistry, vol. 181, 1989, pp. 182-189.
Heimgartner et al, Biochem. J. vol. 267, 1990, pp. 585-591.
J. of Biol. Chemistry, vol. 256 (1980), pp. 11096-11101, Simeral et al.
J. Chem Tech. Biotechnol. 1979, 29, 122-126 (Woodward et al).
Biochem. & Biophys. Res. Comm. 122, No. 3 (1984) Kozulic et al, 1083-1090.
Applied Biochemistry & Biotechnology, vol. 15, 1987, 265-278, Kozulic et al.

Primary Examiner—Howard E. Schain
Attorney, Agent, or Firm—Walter C. Farley; Karen L. Orzechowski

[57] ABSTRACT

A process for the preparation of stabilized glycoproteins without the introduction of foreign molecules. Susceptible monosaccharides covalently attached to the protein part of the molecule undergo periodate oxidation and, after elimination of the remaining periodate, the oxidized glycoprotein is incubated in a buffer under conditions favorable for the reaction between the aldehyde groups generated in the sugar part and the amino acid residues from the protein part. The oxidized carbohydrate chains act as a polyaldehyde crosslinker, with the cross-linking reaction producing intramolecularly and intermolecularly linked derivatives. The amount and size of the intermolecularly linked derivatives are controlled by degree of oxidation and protein concentration. The thermal stability, depends on the degree of oxidation and under optimal conditions is about 10 times better than the stability of native invertase. Additional stabilization of less than optimally oxidized invertase can be achieved by reduction with NaCNBH$_3$.

14 Claims, 6 Drawing Sheets

STABILIZATION OF GLYCOPROTEINS

CROSS-REFERENCES TO RELATED APPLICATIONS

This application is a continuation-in-part of U.S. Pat. application Ser. No. 438,642, filed Nov. 20, 1989, now abandoned.

FIELD OF THE INVENTION

The present invention is directed to a process for preparation of the stabilized glycoproteins. In particular, the present invention is directed to a process for the preparation of stabilized glycoproteins by oxidation and incubation of the glycoprotein.

BACKGROUND OF THE INVENTION

Stability of a protein is very often the critical factor which imposes a limit on practical use of that protein in technological or medical applications. Therefore, much effort has been directed into understanding of those processes that lead to loss of the biological activity. These processes can conveniently be divided into covalent and conformational processes as described by Ahern, T.J., and Klibanov, A.M. in Protein Structure, Folding and Design, (Oxender, D.L., ed. 1986) Alan R. Liss, Inc. New York, pp. 283. The covalent processes include deamidation of asparagine, destruction of disulfide bridges and cleavage of the peptide bonds at aspartic acid residues, whereas conformational processes include changes in the spatial structure of the polypeptide backbone. Stabilized proteins are produced by methods which are able to diminish covalent and/or conformational processes responsible for the inactivation.

There are two general ways to prepare a protein more stable than the original one. By genetic engineering it is possible to exchange one amino acid with the other which is less susceptible to a reaction deleterious for stability or with a new amino acid which contributes to the stabilizing forces. By chemical cross-linking of the original protein it is possible to introduce additional covalent links, which then stabilize the active conformation. There are many reports showing that stabilized proteins can be obtained by both approaches. With respect to the present invention, it should be noted that one of the most widely used protein cross-linking reagents is glutaraldehyde, which is an efficient cross-linker because it always contains polymeric aldehydes. See Peters, K., and Richards, F.M. 46 Ann. Rev. Biochem. 523 (1977).

Glycoproteins are proteins that contain covalently linked sugar chains. The carbohydrate chains are usually not directly involved in biological activity of a glycoprotein, and particularly not in enzymic activity of glycoenzymes. See Tarentino, A.L., Plumer, T.H., and Maley, F. 249 J. Biol. Chem. 818 (1974); Chu, F.K., Trimble, R.B., and Maley, F. 253 J. Biol. Chem. 818 (1978); and Barbaric, S., Mrsa, V., Ries, B., and Mildner, P. 234 Arch. Biochem. Biophys. 567 (1984). We have shown that glycoenzymes can be specifically cross-linked through their carbohydrate chains Kozulic, B., Barbaric, S., Ries, B., and Mildner, P. 122 Biochem. Biophys. Res. Commun. 1083 (1984). Our cross-linking procedure Kozulic, B., Barbaric, S., Ries, B., and Mildner, P. 122 Biochem. Biophys. Res. Commun. 1083 (1984) consisted of two steps. In the first step, susceptible monosaccharides were oxidized by periodate. This resulted in aldehyde groups which in the second step reacted with a bifunctional cross-linker, such as adipic acid dihydrazide.

As demonstrated by electrophoresis, cross-linking with the dihydrazide produces intramolecularly and intermolecularly cross-linked derivatives. See Kozulic, B., Leustek, I., Pavlovic, B., Mildner, P., and Barbaric, S. 15 Appl. Biochem. Biotech. 265 (1987). We have also shown that the cross-linking of carbohydrate chains improves greatly the stability of a glycoenzyme, most likely by increasing the rigidity of its polypeptide backbone. See Kozulic, B., Leustek, I., Pavlovic, B., Mildner, P., and Barbaric, S. 15 Appl. Biochem. Biotech. 265 (1987).

As a control, in that study we have also examined whether intermolecularly cross-linked oligomers were in part the result of Schiff base formation between sugar aldehyde groups and protein amino groups. The results clearly showed that the intermolecularly cross-linked oligomers are mostly the result of adipic acid dihydrazide reaction, although oxidized invertase and acid phosphatase, but not glucose oxidase, without the cross-linker formed a very low amount of oligomers. See Kozulic, B., Leustek, I., Pavlovic, B., Mildner, P., and Barbaric, S. 15 Appl. Biochem. Biotech. 265 (1987). We have also shown that the stabilization effect observed is a result of the cross-linking reaction, since the oxidized invertase and glucose oxidase were essentially as stable as the native enzymes, while oxidized acid phosphatase was less stable than the native enzyme. See Kozulic, B., Leustek, I., Pavlovic, B., Mildner, P., and Barbaric, S. 15 Appl. Biochem. Biotech. 265 (1987). Such results appeared reasonable, since the presumed linkage (Schiff base) between the oxidized sugar and the protein part is reversible. Accordingly, at that time the possibility of glycoprotein stabilization only by periodate oxidation was regarded as inapplicable. This assumption was supported by the results in Woodward, J. and Wiseman, A. 29 J. Chem. Tech. Biotechnol. 122–126 (1979), wherein oxidized invertase showed no increase in stability.

Woodward and Wiseman, in their paper on stabilization of invertases, considered the possibility of Schiff base formation but, as well as Kozulic et al Kozulic, B., Leustek, I., Pavlovic, B., Mildner, P., and Barbaric, S. 15 Appl. Biochem. Biotech. 265–278 (1987) they concluded (page 125, first paragraph): "It is assumed that these aldehyde groups of the mannan moiety did not cross-link with amino groups of the protein moiety since there was no effect on thermal stability." Their experimental data clearly showed (Table 1) that the inactivation constant of the native and oxidized invertase was identical (0.22 min$^{-1}$).

Accordingly, there is no indication in the prior art that periodate oxidation followed by an incubation of the oxidized glycoprotein can result in better stability, and therefore the 10-fold increase in stability now discovered by the applicants was totally unexpected.

A question arises as to how the findings of the present invention could be reconciled with the experimental data in the prior art discussed above. In relation to Applicants' own work, in Kozulic, B. Leustek, I., Pavlovic, B., Mildner, P., and Barbaric, S., 15 Appl. Biochem. Biotech. 265–278 (1987) we did not investigate in detail the properties of fully oxidized glycoenzymes because they formed partially insoluble polymers after addition of adipic acid dihydrazide. Concerning the work of Woodward and Wiseman, after careful reading of their experimental procedures (page 123, paragraph 2.2.5.) Applicants have found an important difference which explains the discrepancy in the experimental results. Specifically, (paragraph 2.2.5. lines 2–3), Woodward et al stopped the periodate oxidation reaction by addition of ethylene glycol. Periodate reacts with ethylene glycol to form formaldehyde. As one of the most reactive aldehydes, formaldehyde reacts with protein amino groups to form an imine which can further react with another amino group:

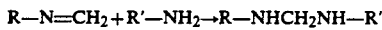

$$R-NH_2+HCHO=R-N=CH_2$$

$$R-N=CH_2+R'-NH_2\rightarrow R-NHCH_2NH-R'$$

Since this reaction was allowed to proceed 1 hour (paragraph 2.2.5. line 3), there was most likely no free amino group left to react with the aldehyde groups formed in the mannan moiety. Therefore, no stabilization effect could be observed.

From the above discussion it is clear that a choice of correct experimental conditions is of utmost importance, because apparently minor modifications can cause a profound effect. This situation is not uncommon, as exemplified by a case where a small change in reaction conditions caused a significant effect. Accordingly, both Thorpe et al. and Casellas et al. U.S. Pat. No. 4,911,912 have treated ricin with periodate in the presence of sodium cyanoborohydride, but Casellas et al have obtained unexpectedly better results when, instead of the whole molecule, only the ricin A chain was treated at a higher pH for a longer time ('912 column 23 and 24).

However, after full apprehension of the idea that an oxidized carbohydrate chain of a glycoprotein may act as an efficient intramolecular cross-linker due to its polyaldehyde character, we have decided to perform more detailed experiments. Unexpectedly, they indicated that certain irreversible linkages were formed after a longer incubation of strongly oxidized glycoproteins. In addition, the new derivatives were found to be much more stable than the native enzyme.

SUMMARY OF THE INVENTION

The present invention is directed to a process for the preparation of stabilized glycoproteins. The process involves the periodate oxidation of the susceptible monosaccharides covalently attached to the protein part of the molecule. Following elimination of iodate and remaining periodate, the oxidized glycoprotein is incubated in a buffer under conditions favorable for its stability and for the reaction between the aldehyde groups generated in the sugar part and the amino acid residues from the protein part. At the end of incubation, if desired, the modified glycoprotein is reduced with a suitable reducing agent, such as $NaCNBH_3$ or $NaBH_4$.

BRIEF DESCRIPTION OF THE DRAWINGS

In the Drawings:

FIG. 1 depicts a 3–30% polyacrylamide gradient gel run under non-denaturing conditions showing invertase treated with different amounts of periodate as described in Example 1;

FIG. 2 depicts a 3–30% polyacrylamide gradient gel run under denaturing conditions showing the same invertase samples described in FIG. 1;

FIG. 3 is a plot of remaining invertase activity after incubation, with the curves representing the different samples described in Example 1;

FIG. 4 depicts a 3–30% polyacrylamide gradient gel run under non-denaturing conditions showing invertase samples incubated after oxidation at different protein concentrations specified in Example 2;

FIG. 5 depicts a 3–30% polyacrylamide gradient gel run under denaturing conditions showing the same invertase samples described in FIG. 4;

FIG. 6 is a plot of remaining invertase activity after incubation, with the curves representing different samples described in Example 2;

FIG. 7 depicts a 3–30% polyacrylamide gradient gel run under non-denaturing conditions showing invertase samples treated before incubation with hexanoic acid hydrazide as described in Example 5;

FIG. 8 depicts a 3–30% polyacrylamide gradient gel run under denaturing conditions showing invertase samples treated before incubation with hexanoic acid hydrazide as described in Example 5;

FIG. 9 depicts a 3–30% polyacrylamide gradient gel run under non-denaturing conditions showing invertase samples treated at different times with hexanoic acid hydrazide as described in Example 5; and FIG. 10 is a plot of remaining invertase activity after incubation, with the curves representing different derivatives described in Example 6.

DETAILED DESCRIPTION OF THE INVENTION

The present invention is directed to a process for the preparation of stabilized glycoproteins. The glycoproteins are stabilized by intermolecular and/or intramolecular reactions between the aldehyde groups in the carbohydrate residues of the glycoprotein molecule and the active groups of the amino acids form the polypeptide moiety of the same glycoprotein.

The fist step of the process of the present invention is the formation of aldehyde groups by periodate oxidation of the glycoprotein moiety. The periodate oxidation must be performed in the absence of any species or reagents that are able to reduce the aldehyde groups.

The second step of the process is eliminating the iodate formed during the periodate oxidation, and any unreacted periodate, from the oxidized glycoprotein without quenching or stopping the periodate oxidation process with the addition of any small molecular weight diol such as glycol.

The third step is incubation of the oxidized glycoprotein in the absence of any species or reagent able to react with the aldehyde groups or with amino acid side chains of the glycoprotein in order to effect formation of covalent bonds between the aldehyde groups and the reactive groups of amino acids of the same glycoprotein.

For a successful glycoprotein stabilization according to the process disclosed in this application it is important to employ specific procedures and characteristics, including the following:

i) to use an optimal periodate concentration, in terms of moles of periodate per mole of the protein bound sugar;

ii) perform periodate oxidation in the dark under conditions (time, pH, temperature, buffer) optimal for each individual glycoprotein;

iii) not to destroy the excess of periodate by any compound whose oxidation products can react with aldehyde groups or amino acid residues, and;

iv) incubate the oxidized glycoprotein under optimal conditions (pH, temperature, time) to effect formation of linkages between the aldehydes and amino acid residues.

From the above considerations, it is clear that the process of the present application is different from the processes described in the prior art. Even in those cases in the prior art where periodate oxidation was done in the absence of any species able to react with the aldehydes or protein amino groups, the third step of the instant process, that is the incubation to form linkages between the aldehydes and reactive groups from the polypeptide moiety, was not carried out. Regarding the glycoprotein stabilization process of Kozulic, B., Leustek, I., Pavlovic, B., Mildner, P., and Barbaric, S., in the second step of that process, addition of adipic acid dihydrazide immediately followed elimination of periodate by gel filtration and therefor that process is different from the instant process.

At present, it is not possible to predict optimal process parameters for each particular glycoprotein because little is known about spatial arrangement of sugar chains in most glycoproteins and even less is known about flexibility of these chains after oxidation. Furthermore, a stabilization effect will be achieved only if on the polypeptide there is a reactive group, such as lysine amino group, spatially close enough to react with the formed aldehyde. Moreover, we do not know whether the aldehydes formed may discriminate between N-terminal and lysine amino groups and whether they react with other groups of amino acid side chains, such as guanidine, hydroxyl (especially from tyrosine), sulfhydryl and imidazole. In the prior art, the reaction mostly discussed has been a Schiff base, which is reversible. The experimental results disclosed in present application demonstrate, for the first time to the best of Applicants' knowledge, that some bonds are not reversible by an alkyl hydrazide as would be the case with a Schiff base. Therefore, at least a part of the stabilization effect disclosed in the present application comes from linkages other than Schiff bases.

The periodate oxidation is conducted under conditions that cause formation of aldehyde groups with retaining as much as possible of the original biological activity of the glycoprotein molecule. The optimal periodate concentration for formation of aldehyde group will be similar for all glycoproteins, however, inactivation due to unspecific oxidations of amino acids will depend upon the particular glycoprotein. Since it is important to retain as much of the original glycoprotein activity as possible, the optimal periodate concentration will be different for each particular glycoprotein. Preferably, the molar ratio of periodate to sugars in from about 0.05 : 1 to about 10 : 1. The molar ratio is more preferably from about 0.1 : 1 to about 2 : 1, and most preferably is about 0.3 : 1 to about 1 : 1.

The periodate oxidation is preformed in the dark and is preferably conducted at a pH range of from about 2 to about 11, more preferably from about 3 to about 8, and most preferably from about 4 to about 6. The temperature should be from about 0° C. to 40° C., more preferably from about 0° C. to 25° C., most preferably from about 0° C. to 4° C. The periodate oxidation is preferably conducted for about 5 minutes to about 48 hours, more preferably from about 5 minutes to about 24 hours, and most preferably from about 1 hour to about 24 hours.

In determining the specific periodate oxidation conditions, it should be kept in mind that, in general, non-specific oxidations are more pronounced at pH values above neutrality, at elevated temperatures and long lasting oxidations. Therefore, if a particular glycoprotein is highly susceptible to unspecific oxidation, it is preferable to oxidize the glycoprotein at a lower periodate concentration for a relatively long time, in the dark at 0° C. to 4° C. at a slightly acid pH. For glycoproteins that are not as susceptible, the glycoprotein can be oxidized for a relatively short time with a high concentration of periodate, but again in the dark at room temperature or below room temperature.

After completion of the formation of the aldehyde groups in the periodate oxidation, the remaining unreacted periodate and the iodate formed during the periodate oxidation process are eliminated from the glycoprotein by any suitable means. Elimination of the remaining periodate can be done chemically, for example by addition of arsenite or sulfite. However, gel filtration is preferred because the added reagents may interfere in subsequent steps or may be undesirable during final applications. Periodate and iodate can be eliminated also by dialysis or ultrafiltration, which are time consuming and therefore less preferred than gel filtration.

The incubation conditions depend upon the particular glycoprotein and will be chosen to stabilize the conformation that will yield the desired protein biological activity. It is known that the biological activity of a protein is pH dependent. The incubation can be performed at different pH values because, as shown here, the aldehydes react with amino acid side chains over a broad pH range. Once a pH value close to the pH optimum for the biological activity is chosen, then temperature and time are interrelated. As in any other chemical reaction, the rate of reaction between the aldehydes and amino acid side chains is faster at a high temperature. In addition, the rate of reaction is also faster because flexibility and mobility of the oxidized polysaccharide chains increase with temperature and thus the incubation time can be short. However, incubation at a high temperature increases also the flexibility and mobility of the polypeptide backbone. This may cause a change in conformation and thus inactivation, or newly formed linkages may be formed after the change in conformation, again leading to partial or complete inactivation. Stabilization of a new conformation may also change substrate specificity. It is clear therefore that the optimal time and temperature for stabilization will need to be determined for each particular conformation. For glycoproteins that are moderately stable in their native form, incubation at room temperature for about two days is usually satisfactory, as discussed here.

From the foregoing, it is clear that the process of the present application can be used advantageously because it is simple, inexpsensive and does to require an organic molecule to act as a cross-linker.

EXAMPLE 1

In Example 1 the influence of the degree of oxidation on the oligomer formation and stability was studied.

Invertase (from Sigma) at concentration of 1.5 mg/ml in 0.1 M sodium acetate pH 4.6, was oxidized with different amounts of the freshly prepared sodium periodate solutions. The quantity of sodium periodate added is expressed as a molar percentage to the neutral sugars present in invertase. Neutral sugars were assayed by the orcinol-sulfuric acid method, described in Francois, C., Marshal, R.D., and Neuberger, A., 83 Biochem. J. 335 (1962) with mannose as a standard.

The enzyme was oxidized at 4° C. for 24 hours in the dark. Iodate and the remaining periodate were eliminated by gel filtration on a small column (1.5×8 cm) filled with Sephadex G-25 and equilibrated in the same acetate buffer. The oxidized glycoprotein solutions were concentrated to the original protein concentration and incubated at room temperature for two days. They were then analyzed by electrophoresis in the 3-30% polyacrylamide gradient gels under nondenaturing (FIG. 1) or denaturing (SDS) conditions (FIG. 2). Electrophoresis buffer was 0.1 M Tris-borate pH 8.3, with 1 mM EDTA. For SDS electrophoresis, 0.1% SDS was added to the buffer and electrophoretically introduced into 330% gradient gels before application of the samples.

Figure 2:
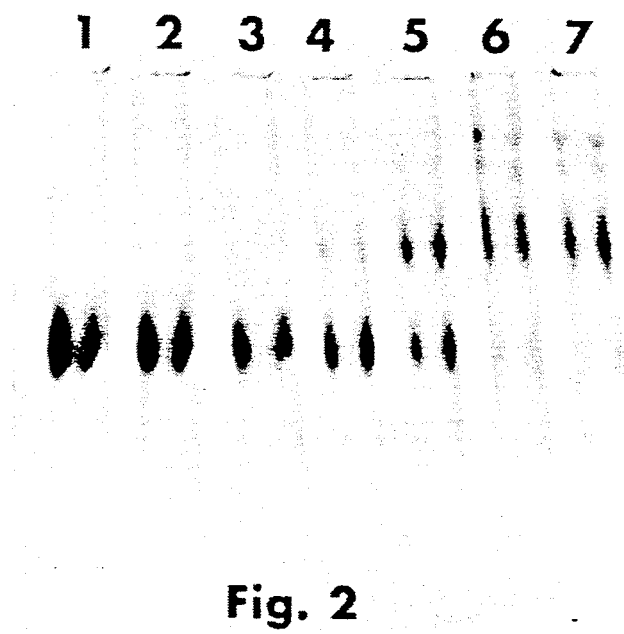

FIG. 1 shows untreated dimeric invertase (lane 1), and invertase oxidized with 5% periodate (lane 2), 10% (lane 3), 20% (lane 4), 50% (lane 5), 100% (lane 6) and 200% (lane 7). As can be seen, the quantity of oligomers (produced by intermolecular cross-linking) increases up to 100% added periodate. No further increase is noticed at 200% periodate. These results indicate that, under the conditions specified, no additional and reactive aldehyde groups are produced when periodate is added in a molar amount exceeding that of mannose, because maximal formation of oligomers is achieved at 100% or less periodate.

FIG. 2 shows the invertase subunit (lane 1) and the oxidized invertase derivatives in the same order as described under FIG. 1. There is very little intersubunit cross-linking (leading to the dimer represented by the upper band) at 5% and 10% periodate oxidation (lanes 2 and 3). However, at 100% (and 200%) periodate oxidation most invertase subunits are cross-linked, a larger fraction of subunits into the dimer and the smaller into the high molecular weight oligomers (lanes 6 and 7).

The results presented in FIGS. 1 and 2 thus demonstrate that an oxidized glycoprotein molecule can react with another such molecule and form oligomers (FIG. 1). These results also demonstrate that an oxidized sugar chain from one polypeptide (subunit) can react with the other polypeptide (subunit) present in the same dimeric invertase molecule (FIG. 2). We assume that, due to even more favorable steric conditions, an oxidized sugar chain reacts also with polypeptide to which it is bound (this would be intrasubunit cross-linking), but such derivatives cannot be detected by the electrophoretic method used here.

Figure 3:
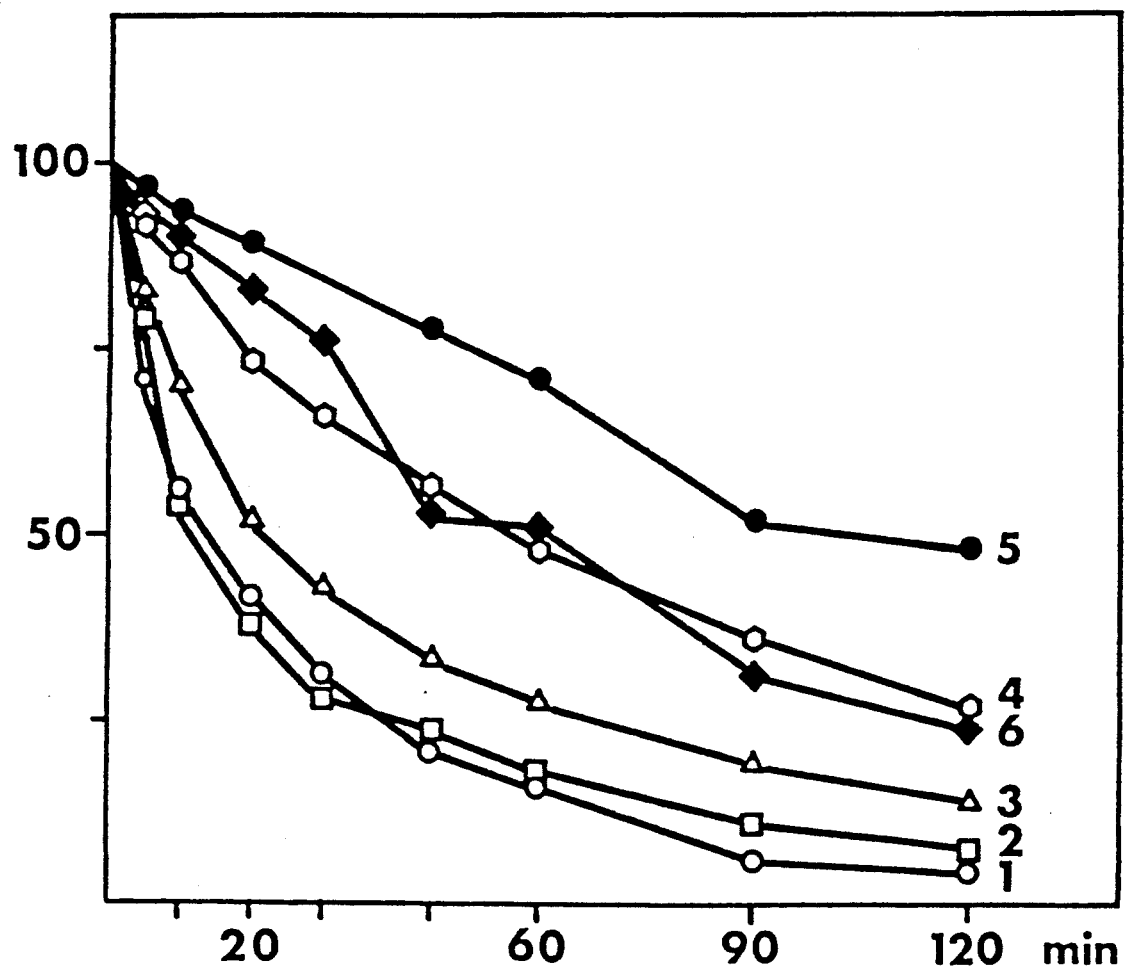

We have investigated the thermal stability of invertase oxidized to various degrees by sodium periodate. Invertase derivatives were incubated at 63° C. and at the times indicated, portions of the enzyme solution were removed, cooled by dilution in a chilled buffer and the remaining invertase activity was measured at 30° C., as described in Bernfeld, P. 12 Adv. Enzymol. 379 (1951). the remaining activity was plotted against time intervals (FIG. 3). The curves represent native invertase (curve 1), invertase oxidized with 10% periodate (curve 2), 20% (curve 3), 50% (curve 4), 100% (curve 5), and 200% (curve 6). As can be seen, the thermal stability of invertase increases with the degree of oxidation, from 10 to 100% periodate added (curves 5). At 200% oxidation (curve 6) the stability is lower. Under the best oxidation conditions (curve 5), the enzyme is about 10 times more stable than the native invertase, as determined from the time required for 50% inactivation.

EXAMPLE 2

Example 2 was directed to the study of the influence of the protein concentration on the formation and stability of the cross-linked derivatives.

Invertase at different concentrations was oxidized with 100% periodate and further treated under conditions specified in Example 1. The samples were analyzed by polyacrylamide gradient (3-30%) gel electrophoresis under nondenaturing (FIG. 4) and denaturing (FIG. 5) conditions. Untreated invertase was applied to this gel (lane 2), as was the enzyme oxidized at 0.33 mg/ml (lane 3), 1.0 mg/ml (lane 4), 2.0 mg/ml (lane 5), 4.5 mg/ml (lane 6) and 9.0 mg/ml (lane 7). Standard proteins were applied to lane 1.

As expected, the amount of oligomers increases with protein concentration, and at the concentrations above 2 mg/ml there is very little of the native dimer left and at 9 mg/ml partially insoluble derivatives are formed.

Figure 4:
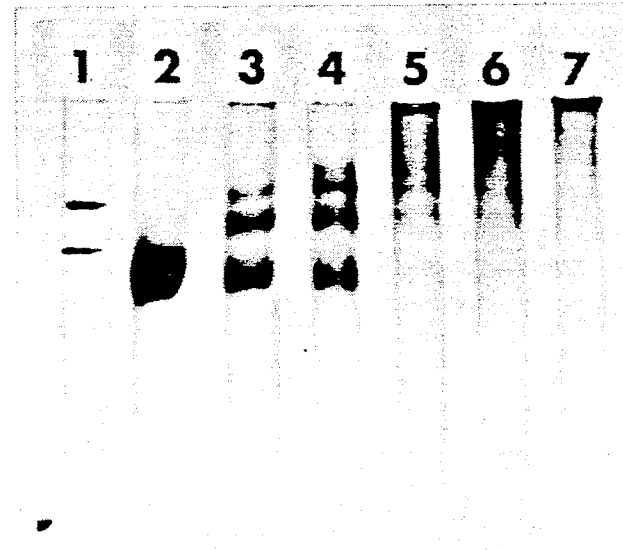
Figure 5:
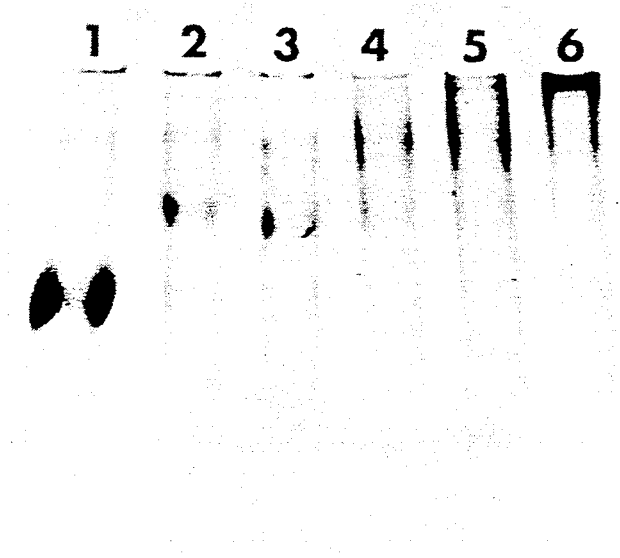

SDS electrophoresis (FIG. 5) of the same samples as in FIG. 4, shows that practically every invertase subunit is linked to another one a protein concentrations above 2 mg/ml. At higher protein concentrations (4.5 and 9.0 mg/ml) some oligomers are so large that they cannot enter the gel (FIGS. 4 and 5).

We have further studied the thermal stability of the cross-linked invertase derivatives, prepared at different protein concentrations as described above. The measurements of the remaining invertase activity were done as given in Example 1 U]% '*15*6 shows the stability of native invertase (curve 1) and invertase that was oxidized and, after elimination of any periodate and iodate, inoubated at 0.33 mg/ml (curve 2), 1 mg/ml (curve 3) and 4.5 mg/ml (curve 4).

Figure 6:
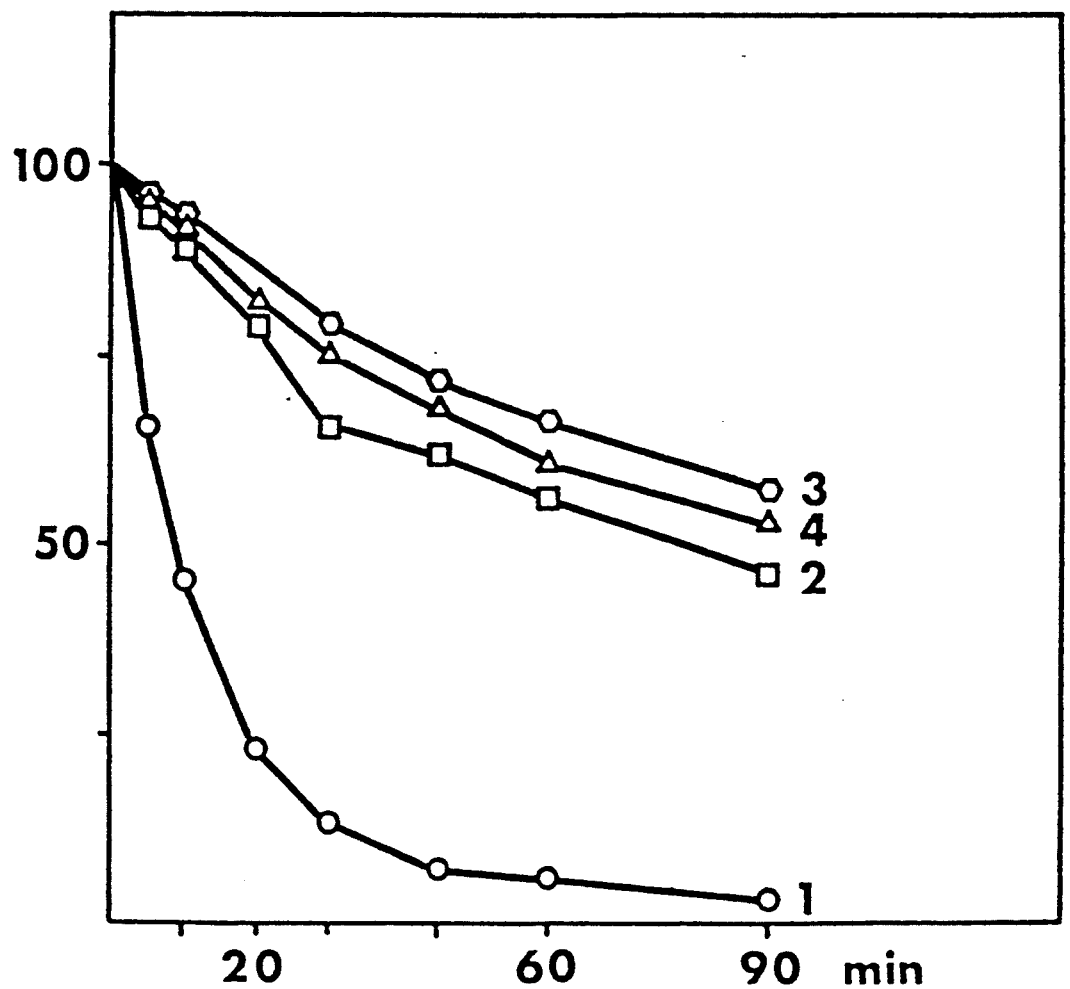

All cross-linked derivatives were much more stable than the native invertase. Moreover, there is very little difference between the stability of derivatives prepared at various protein concentrations (curves 2-4). This finding indicates that the oligomers formed at higher protein concentrations (FIGS. 4 and 5) are not much more thermally stable than the cross-linked dimer. Accordingly, the results of FIGS. 4, 5 and 6 indicate that intramolecular (including intrasubunit) cross-linking is of primary importance in stabilization of the glycoprotein conformation.

EXAMPLE 3

Example 3 was directed to the study of the influence of the oxidation time on oligomer formation and stability.

Invertase was oxidized by periodate (0.5 : 1 molar ratio to sugars) as described in Example 1 except that the oxidation times were 5 minutes and 15 minutes, and 1 hour, 2 hours, 6 hours, 12 hours and 24 hours. After incubation at room temperature for two days, followed by native gradient gel electrophoresis, higher oligomers were barely detectable where the period was 5 minutes long. Intensity of the high molecular weight bands increased gradually with increasing oxidation time. There was only a slight difference between oxidation times of 12 hours and 24 hours. Thermal stability of invertase oxidized for 5 minutes was only marginally better that the stability of the native enzyme, whereas the stability of the enzyme sample oxidized for 12 hours was essentially the same as of that oxidized for 24 hours shown in FIG. 3.

The extent of stabilization clearly depends on oxidation time at a given periodate concentration. However, the oxidation time and periodate concentration can be varied independently, meaning that a short incubation time at a high periodate concentration produces the same number of aldehyde groups as a long incubation at a low periodate concentration. However, it is preferable to use low periodate concentrations for longer times because we have noticed that high periodate concentrations very often cause enzyme inactivation, most likely due to non-Malapradian oxidations.

EXAMPLE 4

Example 4 was directed to a study of the influence of incubation pH on formation of oligomers.

Invertase (3 mg/ml in acetate buffer pH 4.6) was oxidized (0.5 to 1 molar ratio of periodate to sugars) at 0° C. for 12 hours, passed through gel filtration columns equilibrated in different buffers and incubated for 48 hours. The pH values of the incubating solutions were 3.8, 4.6, 5.4, 6.2, 7.0, 8.0 and 9.5. Each sample was analyzed by gradient gel electrophoresis under nondenaturing conditions. At all pH values tested there were intense bands corresponding to high molecular weight oligomers. The size of the oligomers was higher at pH 3.8, 4.6, 8.0 and 9.0 than at pH 5.4, 6.2 and 7.0.

The above result shows that the aldehydes formed by periodate oxidation are able to react with the amino acid side chains at pH values across a broad range. Accordingly, for a particular glycoprotein the incubation pH may be chosen so that it corresponds to, or is close to, the pH value optimal for stability and/or activity of the native glycoprotein. In this way the newly formed linkages will stabilize the native conformation.

EXAMPLE 5

Example 5 was directed to the study of the influence of the addition of hexanoic acid hydrazide on formation of the cross-linked invertase derivatives.

Invertase (2 mg/ml) in 0.1 M sodium acetate buffer pH 4.6 was oxidized with 100% periodate. After elimination of any periodate and iodate, one part was treated with hexanoic acid hydrazide (twice the molar amount of periodate). The other part was not treated. Both parts were incubated for two days at room temperature. The samples were then analyzed by electrophoresis in 3-30% gradient gels under nondenaturing conditions (FIG. 7) and denaturing conditions (FIG. 8).

Figure 7:
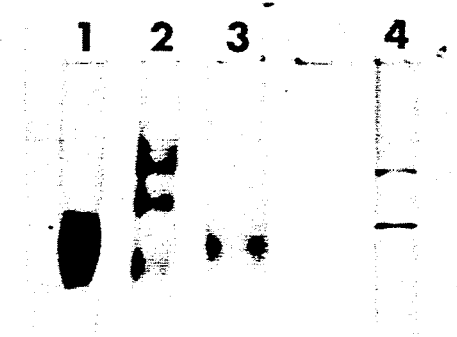

In FIG. 7, native invertase was applied to lane 1, the oxidized enzyme without the monohydrazide to lane 2 and the oxidized enzyme with the monohydrazide to lane 3. Standard proteins were applied to lane 4.

As can be seen, addition of hexanoic acid hydrazide almost completely prevented the formation of invertase oligomers (lane 2 versus lane 3), and the derivative with hexanoic acid hydrazide migrated to a similar distance as did the native invertase (lane 3 versus lane 1).

Figure 8:
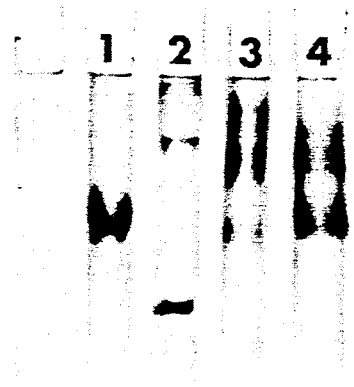

FIG. 8 shows the same samples as those applied to FIG. 7 but run under denaturing conditions. Untreated invertase was applied to lane 1, standard proteins to lane 2, oxidized invertase to lane 3 and oxidized invertase treated with hexanoic acid hydrazide to lane 4.

In both oxidized samples (lanes 3 and 4), there is one band migrating the same distance as the invertase subunit (lane 1). The intensity of this band is stronger in lane 4, demonstrating that hexanoic acid hydrazide prevented formation of some intramolecular cross-links between invertase subunits. However, at the concentration used, this monohydrazide was not able to completely prevent the formation of cross-links between the two subunits, because some derivatives migrated as a dimer (lane 4). An alternative explanation is that hexanoic acid monohydrazide was not able to reverse certain linkages that were formed before it could react with the free aldehyde groups (or the Schiff bases).

Figure 9:
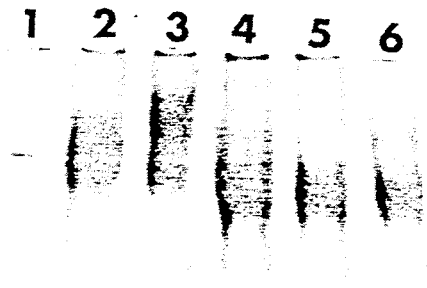

We have further attempted to see whether hexanoic acid hydrazide could reverse the intermolecular cross-links. FIG. 9 shows a native 3-30% polyacrylamide gradient gel, containing the following samples. Lane 1 contains standard proteins; lane 2, native invertase; lane 3, oxidized invertase (100%, incubated for two days); lane 4, oxidized invertase to which hexanoic acid hydrazide was added before the periodate and iodate elimination step; lane 5, oxidized invertase to which hexanoic acid hydrazide was added immediately after the periodate and iodate elimination step and lane 6, oxidized invertase to which hexanoic acid hydrazide was added 48 hours after the periodate and iodate elimination step.

As shown also in the previous figures, the oxidized invertase formed oligomers (lane 3). The addition of hexanoic acid hydrazide before desalting prevented partially and after desalting almost completely the formation of intermolecular cross-links (lane 4 versus lane 5). This is apparently a contradicting result because earlier addition should have a better preventive effect. However, unreacted periodate reacts with a hydrazide group (our unpublished observation), and the resulting lower concentration of the monohydrazide in the nondesalted sample is a likely explanation for the weaker preventive effect (lane 4 versus lane 5). Moreover, hexanoic acid hydrazide added after 48 hours was able to partially reverse the cross-links (lane 6 versus lane 3), but some oligomers still persisted (lane 6 versus lane 5).

The results presented in FIGS. 7, 8 and 9 strongly indicate that certain stable bonds are formed after a prolonged incubation of the oxidized glycoproteins. Such bonds may be similar to ketoamine linkages resulting from the Amadory rearrangement of the Schiff base, which is initially formed from a sugar aldehyde and a primary amino group. See Mori, N., and Manning, J.M. 152 Anal. Biochem. 396 (1986). However, we do not know which bonds lead to the stable invertase derivatives. They may mostly come from the Amadory or another rearrangement of Schiff bases or from completely new type of reactions involving the aldehydes and other amino acid side chains.

EXAMPLE 6

Example 6 studies the influence of the addition of a monohydrazide and a reducing reagent on stability of the oxidized invertase.

Figure 10:
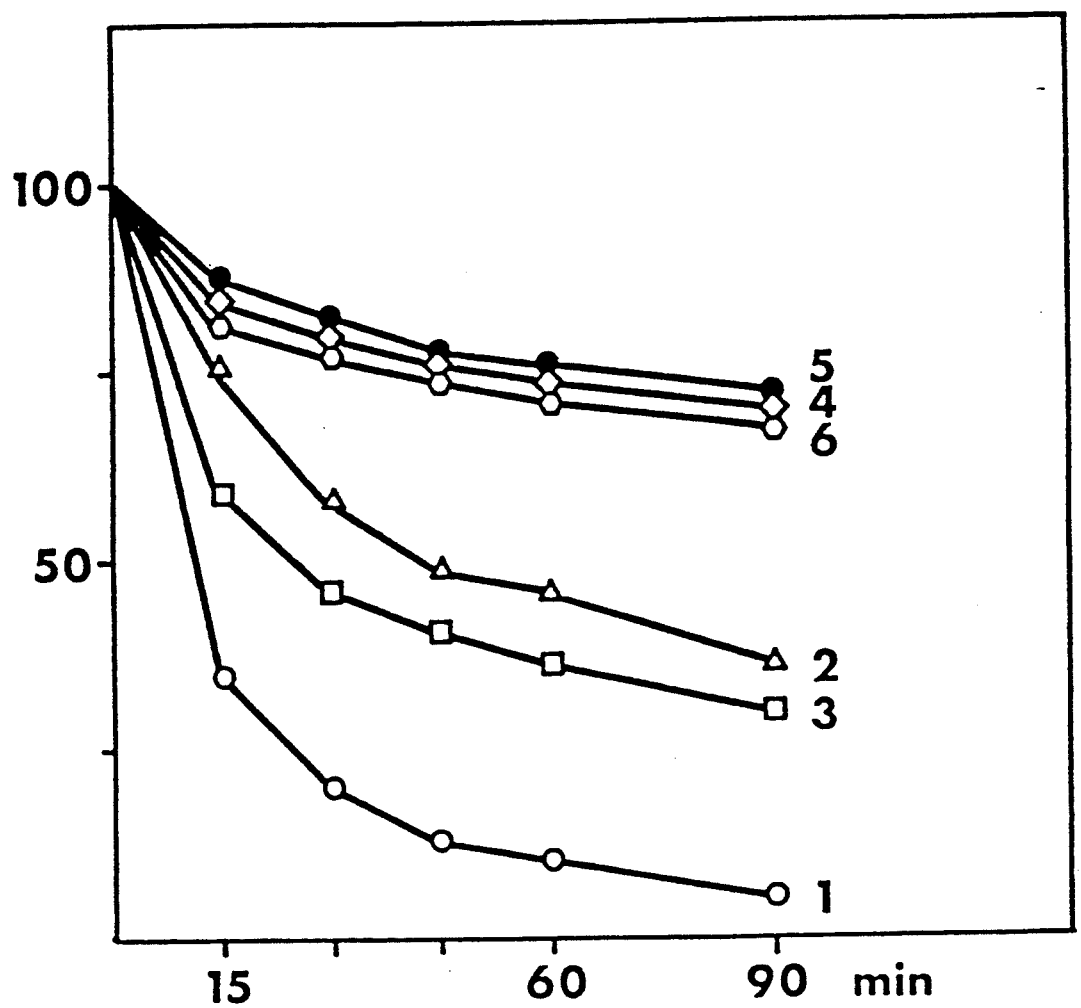

FIG. 10 shows the thermal stability (63° C.) of various invertase derivatives. Native invertase is represented by curve 1. Invertase (2 mg/ml) was oxidized with 50% periodate, desalted and left for two days (curve 2). The same sample of oxidized invertase after two days was treated with hexanoic acid hydrazide (curve 3). The oxidized invertase that was cross-linked with adipic acid dihydrazide Kozulic, B., Leustek, I., Pavlovic, B., Mildner, P., and Barbaric, S. 15 Appl. Biochem. Biotech. 265 (1987) is represented by curve 4. The oxidized invertase was reduced (20 mM NaCNBH$_3$, pH 6.5, 4 hours) after two days (curve 5).

To the reduced invertase, hexanoic acid hydrazide was added (curve 6).

The oxidized enzyme is more stable than the native one (curve 2 versus 1). Further, the oxidized enzyme becomes less stable after treatment with a monohydrazide (curve 2 versus 3), indicating that towards hydrazide reversible bonds also participate in stabilization of the active conformation. In accordance with our previous findings Kozulic, B., Leustek, I., Pavlovic, B., Mildner, P., and Barbaric, S. 15 Appl. Biochem. Biotech. 265 (1987), the cross-linking of the oxidized enzyme with a dihydrazide increases its thermal stability (curve 4 versus 2). The treatment with NaCNBH$_3$ (resulting in reduction of Schiff bases to the stable secondary amines) greatly improved the thermal stability (curve 5 versus 2). Subsequent addition of the monohydrazide to the reduced sample showed practically no effect (curve 6 versus 5).

These results indicate that thermal stability is highly dependent on the number of newly formed stable bonds. This number can be increased by a subsequent treatment, such as cross-linking with a dihydrazide or reduction with NaCNBH$_3$. However, it should be noted that 100% oxidized invertase, without any further treatment, showed a similar thermostability as did the subsequently treated enzyme (figure 3 versus 10).

The results presented herein (FIGS. 3, 6 and 10) clearly demonstrate that a stabilized glycoprotein shows a better performance under harsh conditions (high temperature) than the original one. Thus, due to its improved stability much more invert sugar will be produced by the cross-linked invertase under conditions (about 50° to 60° C.) often used in industrial applications.

EXAMPLE 7

Example 7 was directed to the study of the influence of the incubation time on the stability of the glycoprotein.

Invertase was oxidized with periodate at 1 : 1 molar ratio to protein bound sugars as described in Example 1.

After removal of iodate and periodate by gel filtration the enzyme was incubated at room temperature for one hour. Its thermal stability at 63° C. was about 30% higher than the stability of the native enzyme.

Comparison of this result with the one shown in FIG. 3 indicates that stability increases with time at a given temperature. The incubation time and temperature may be varied independently. At higher temperatures the reaction of aldehyde groups is faster and therefore the incubation time can be shorter. On the other hand, thermal inactivation is also faster and therefore for a particular glycoprotein a compromise needs to be found between the incubation time and temperature. Room or slightly higher temperature is preferable for most glycoproteins.

Examples 8 and 9 studied the stabilization of other glycoproteins.

EXAMPLE 8

Glucose oxidase (5.6 mg/ml in 0.1 M phosphate buffer pH 5.8) was oxidized for 5 hours at 4° C. with 1 : 1 molar ratio of periodate to sugars. After gel filtration the enzyme was incubated at room temperature for 24 hours. Stability of the enzyme was tested against denaturation by 4 M urea. The enzyme was about 40% more stable than native glucose oxidase. Moreover, the stability against denaturation at high pH was also tested. At pH 11.5, the treated enzyme exhibited about 30% better stability than the native enzyme. Thus, the stabilization of glycoprotein conformation by the process disclosed here can improve glycoprotein stability also against other agents causing inactivation, exemplified by high pH and urea.

EXAMPLE 9

Horse radish peroxidase (5 mg/ml in acetate buffer pH 5.0) was oxidized with 10 mM sodium periodate for 2 hours at 0° C. in the dark. The sample was then passed through a gel filtration column. The enzyme was added into a 5% solution of defatted milk (in 0.1 M sodium acetate buffer pH 4.7 containing 0.2 M sodium chloride) and incubated at 4° C. for 2 months. The enzyme activity was periodically checked and after two months there was about 90% of the activity left. This result shows that the incubation time may be very long and that a stabilized enzyme may be incubated in the presence of other proteins.

The results of the above examples demonstrates that different glycoproteins can be stabilized by the process disclosed here. That can be explained by the fact that periodate forms aldehyde groups in all polysaccharides, including sugar chains present on both high-mannose and complex type glycoproteins. The aldehyde groups are of similar reactivity, as demonstrated by Heimgartner, U., Kozulic, B., and Mosbach, K., 267 Biochem. J. 585–591 (1990) where after periodate oxidation sugar chains in a complex type glycoprotein have been cross-linked by dihydrazides in a way similar to cross-linking of the high-mannose type glycoproteins.

The stabilization of glycoproteins only by periodate oxidation, and eventually by reduction but not cross-linking with a dihydrazide, is more suited for those glycoproteins that do not lose much activity upon a strong oxidation. This approach is also advantageous in those applications of the stabilized derivatives in which the presence of a foreign molecule, such as a dihydrazide cross-linker, is not desirable.

We claim:

1. A process for the preparation of a stabilized glycoprotein, wherein the glycoprotein is stabilized by intermolecular and/or intramolecular reactions between aldehyde groups in carbohydrate residues of the glycoprotein molecule and active groups of amino acids from the polypeptide moiety of the same glycoprotein, the process comprising the steps of forming the aldehyde groups by periodate oxidation, wherein the periodate oxidation is performed in the absence of any species or reagent able to reduce the aldehyde groups;

eliminating iodate and unreacted periodate from the oxidized glycoprotein by a process excluding a reaction with any small molecular weight diol; and incubating the oxidized glycoprotein in the absence of any species or reagent able to react with the aldehyde groups or with amino acid side chains of the glycoprotein in order to effect formation of covalent bonds between the aldehyde groups and the reactive groups of amino acids of the same glycoprotein.

2. A process according to claim 1, wherein the molar amount of added periodate is in the range of from 5 to 200% of the monosaccharides attached to the protein.

3. A process according to claim 2, wherein the periodate oxidation is performed in the dark in a buffered solution with a pH value from 2 to 11.

4. A process according to claim 2, wherein periodate oxidation is performed for an interval between about 5 minutes and about 24 hours.

5. A process according to claim 2, wherein periodate oxidation is performed at or below room temperature.

6. A process according to claim 2, wherein the low molecular weight molecules are eliminated after the periodate oxidation by gel filtration.

7. A process according to claim 1, wherein the incubation of the oxidized glycoprotein is performed at a pH value equal to a pH value optimal for stability of the unoxidized glycoprotein.

8. A process according to claim 7, wherein the oxidized glycoprotein is incubated in a solution with a pH value in the range of about 2 to about 11.

9. A process according to claim 7, wherein the oxidized glycoprotein is incubated at a temperature in the range of about 0° to about 80° C.

10. A process according to claim 7, wherein the oxidized glycoprotein is not further treated before an application.

11. A process according to claim 7, wherein the oxidized glycoprotein is further treated before an application.

12. A process according to claim 11, wherein the further treatment includes a reduction of the bonds formed in the oxidized glycoprotein.

13. A process according to claim 11, wherein the further treatment comprises a reduction with $NaCNBH_3$ or $NaBH_4$.

14. A stabilized glycoprotein prepared according to the process of claim 1.

* * * * *